United States Patent [19]

Burleson

[11] Patent Number: 4,640,782
[45] Date of Patent: Feb. 3, 1987

[54] METHOD AND APPARATUS FOR THE GENERATION AND UTILIZATION OF OZONE AND SINGLET OXYGEN

[75] Inventor: James C. Burleson, Friendswood, Tex.

[73] Assignee: Ozo-Tek, Inc., Houston, Tex.

[21] Appl. No.: 711,257

[22] Filed: Mar. 13, 1985

[51] Int. Cl.$^4$ ............................................. C02F 1/78
[52] U.S. Cl. .................................. 210/748; 204/176; 210/760; 210/764; 210/192; 210/169; 261/DIG. 42; 261/DIG. 75; 422/28; 422/186.12; 422/186.18
[58] Field of Search ..................... 204/176; 166/267; 210/760, 748, 192, 198.1, 205, 206, 169, 764; 261/DIG. 42, DIG. 75; 422/186.12, 186.18, 22, 28, 29

[56] References Cited

U.S. PATENT DOCUMENTS

| | | | |
|---|---|---|---|
| 1,077,020 | 10/1913 | Walden | 210/760 |
| 3,326,747 | 6/1967 | Ryan et al. | 210/760 |
| 3,421,999 | 1/1969 | Corwin | 210/192 |
| 3,510,265 | 5/1970 | Kawahata | 210/192 |
| 3,867,288 | 2/1975 | Schaefer | 210/760 |
| 3,975,247 | 8/1976 | Stralser | 210/754 |
| 4,049,552 | 9/1977 | Arff | 210/192 |
| 4,172,786 | 10/1979 | Humphrey et al. | 210/760 |
| 4,417,966 | 11/1983 | Krauss et al. | 422/186.18 |

FOREIGN PATENT DOCUMENTS 2102303 2/1983 United Kingdom ............... 210/760

*Primary Examiner*—Peter Hruskoci
*Attorney, Agent, or Firm*—Guy E. Matthews

[57] ABSTRACT

A method and apparatus to kill pathogens with ozone and singlet oxygen. Includes steps of providing a reaction chamber, establishing an elevated electrical force field in the reaction chamber and moving a gas containing normal oxygen ($O_2$) through the chamber to permit ionization and consequent reaction within the gas which converts the oxygen ($O_2$) into constituents of ozone ($O_3$) and singlet oxygen ($O_1$). Next moves gas containing constituents into contact with pathogens to kill pathogens. Invention is applied to sterilize medical instruments and containers, and when applied to human skin surfaces, for treatment of pathogenic infestations.

9 Claims, 4 Drawing Figures

METHOD AND APPARATUS FOR THE GENERATION AND UTILIZATION OF OZONE AND SINGLET OXYGEN

This invention generally relates to the generation and application of ozone ($O_3$) and singlet oxygen ($O_1$) and more particularly relates to improvements in generating the constituents of ozone and singlet oxygen along with methods and apparatus for killing pathogens with these constituents.

BACKGROUND OF THE INVENTION

The purification of water with ozone began in Europe about 1893 when drinking water was purified with an ozone pretreatment system. Now several communities throughout the world use ozone to pretreat drinking water.

Ozone treatment of swimming pool water began in Europe in the early 1950's and has steadily gained acceptance since that time. It is now considered to be one of the most effective water sanitizers available today, even though most health departments regulations in the United States require the pool operator to test for pH and chlorine.

It is not difficult to spot a pool, spa or hot tub where the water has been treated with ozone. The water is crystal clear and there is nothing in the water to make bather's eyes sting. There are no chemical odors.

Ozone ($O_3$) is found commonly in nature and is formed by lightning bolts or other electrical discharge creating a spark. Ozone is also the result of direct ultraviolet radiation from the sun reacting with the planets atmosphere.

Most ozone generated is by the ultraviolet (UV) process where ordinary air is moved through a reaction chamber energized by untraviolet light which splits some oxygen molecules into oxygen atoms. The oxygen atoms quickly react with oxygen molecules to form ozone ($3O_2 + Energy = 2O_3$).

To be effective the ozone air mixture must be thoroughly dissolved into the water which is an equally important step in the total process. The dissolved or dispersed ozone can then react with the bacteria, virus, algae, protozea and other contaminants and pathogens before the water is returned to a pool/spa or the like.

Government agencies (OSHA and the EPA) are watching to insure that ozone systems meet high standards. Some agencies established within the pool and spa industry are writing new guidelines and recommendations to deal with equipment used in pools and spas as well as the purification of the water.

There are many advantages in ozonating various types of aqueous liquids, as later outlined throughout the specification, and there is no doubt that the economic and health advantages of a well designed and quality ozonation system make purification and sterilization a relatively easy requirement to reach.

The predominant prior art showing the generation of ozone illustrates special ultraviolet (UV) equipment which causes naturally occurring oxygen ($O_2$) in the air to disassociate forming two individual oxygen atoms $O_1$ which subsequently combine with additional oxygen molecules to form ozone ($O_3$). The resulting ozone gas is then remixed with water where the disinfection immediately occurs.

The present invention utilizes apparatus which may be referred to as silent electrical discharge apparatus.

The term "silent electric discharge" as used herein generally means an electrical discharge of the silent-type characterized by a relatively high voltage, a relatively low current density and a relatively low gas temperature. Radiation detection devices such as geiger/mueller counters and ionization chambers may be thought of as silent electrical discharge types of apparatus.

It is believed the UV process is not sufficently energetic to release effective amounts of singlet oxygen as does the silent electrical discharge method and apparatus.

The singlet oxygen is readily reactable with all organic materials, including both pathogens and water impurities. Presence of singlet oxygen with the ozone is believed to definitely enhance any sterilization process.

At present no prior art is known for generating ozone and singlet oxygen with the use of such silent electric discharge apparatus particularly when combined with steps of moving the ozone and singlet oxygen constituents into contact with pathogens for sterilization and medical treatment.

Prior art which is known utilizing silent electrical discharge apparatus is U.S. Pat. Nos. 3,475,308; 3,497,436 and 3,518,178. One of the joint inventors in these prior art patents is the inventor of this present invention. To the extent as may be pertinent, these patents are incorporated herein by reference.

OBJECTS OF THE INVENTION

One object of the present invention is to provide a method and apparatus for generating ozone and singlet oxygen which is convenient, inexpensive and efficient.

Another object of the present invention is to produce ozone and singlet oxygen on a continuous basis for continuous treatment of an aqueous liquid.

Another object of the present invention is to produce ozone and singlet oxygen suitable for application to kill pathogens in medical treatment.

Yet another object of the present invention is to produce ozone and singlet oxygen to sterilize various kinds of containers, vessels and piping as become contaminated by various kinds of bacteria, viruses and the like.

SUMMARY OF THE INVENTION

In accordance with the present invention a method and apparatus for producing ozone and singlet oxygen is provided. The method includes the steps of providing a reaction chamber defined between the first area of a first electrical conductor surface and the second area of a second electrical conductor surface and providing a dielectric medium between such first area and such second area which partially fills the reaction chamber. The method next includes establishing an elevated electrical force field in the reaction chamber between the first conductor surface and the second conductor surface and subsequently moving a gas containing normally occurring oxygen ($O_2$) into, through and out of the reaction chamber at a moving rate suitable to permit ionization and consequent reaction within the gas as caused while the gas is within the force field. The force field ionizes the gas which converts the normally occurring oxygen into the constituents of ozone ($O_3$) and singlet oxygen ($O_1$). The method next involves moving the gas while it contains these constituents into contact with selected pathogens for the purpose of allowing the constituents to react with and kill such pathogens.

This method also includes the step of allowing naturally occurring cosmic radiation to pass through the electrical force field and thereby contribute to the ionization. The reaction chamber is formed as an annular chamber defined by a cylindrical body of electrically conductive liquid which forms the first electrical surface, a cylindrical tube of insulative material confining the liquid and forming the dielectric medium, and a cylindrical metal housing enclosing the tube and forming the second electrical surface. The method also includes the step of pumping or otherwise moving the electrically conductive liquid through the tube and thereafter through a Venturi tube and concurrently injecting the gas including the constituents into the Venturi to be thoroughly mixed with the conductive liquid. Apparatus as needed to perform the steps of this method is also provided.

The invention may be applied to sterilize and clean aqueous liquids such as swimming pool water, waste water and sewage systems, potable drinking water, oil well completion fluids, oil well injection fluids, and cooling water such as used in heat exchanger cooling towers, for example.

The gas containing the ozone and singlet oxygen constituents may also be utilized in steps to sterilize medical instruments and containers which become contaminated with bacteria and the like.

The gas containing such constituents may also be used, when applied to human skin surfaces, for sterilization and also for treatment of infestations by competant medical practioners such as athletes foot, jock itch, seborrhea, and other fungal infestations. (These constituents are toxic until dissipated).

DESCRIPTION OF THE PREFERRED EMBODIMENTS

Figure 1:
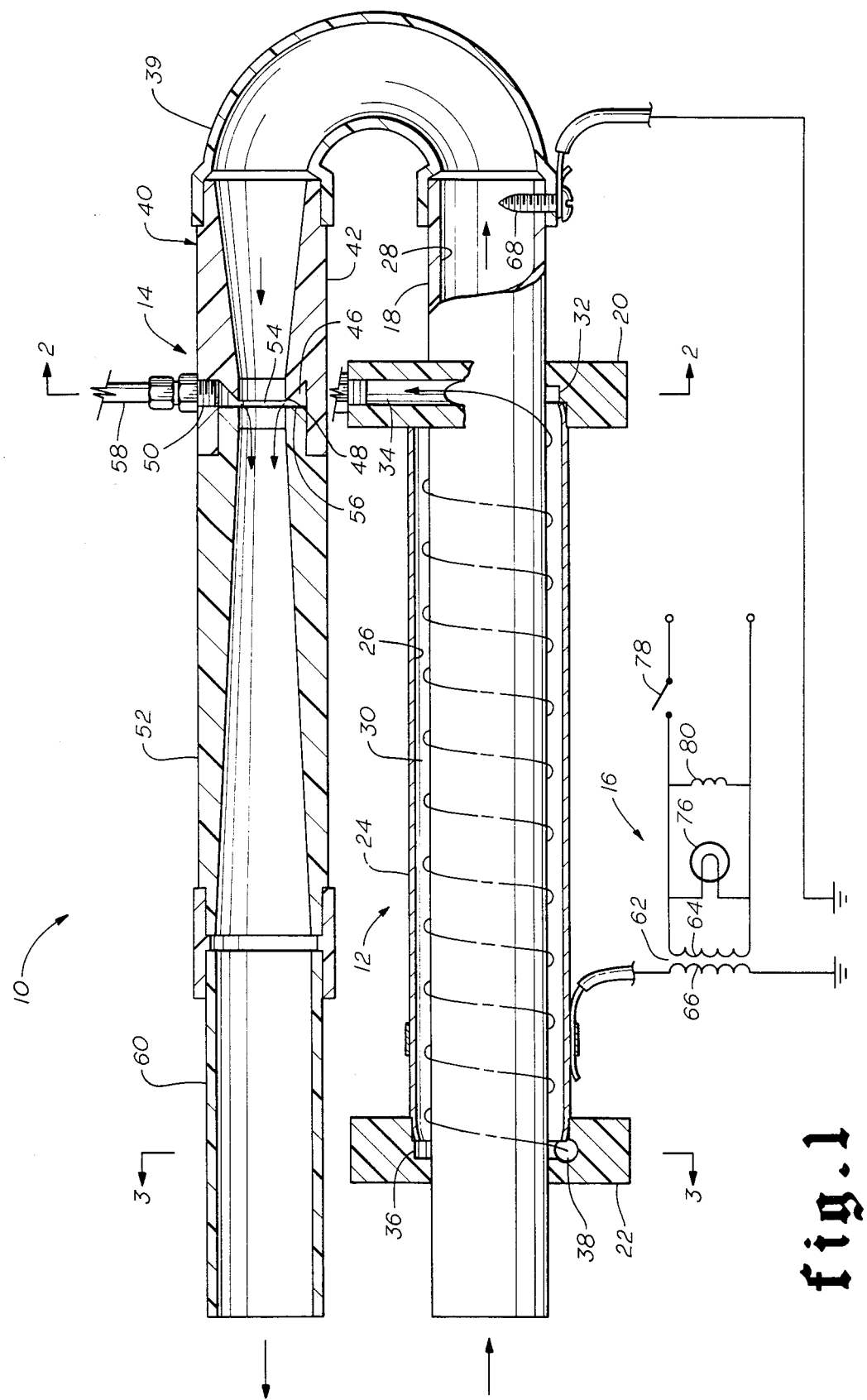
FIG. 1 is a side elevational section taken along 1—1 of FIGS. 2 and 3 showing the ozone generator including the reactor and a schematic illustration of the electrical system.

The numeral 10 designates the entire ozone generator apparatus including the reactor 12, the Venturi mixer 14 and the electrical system 16. As shown, an insulated flow tube 18 extends through reactor 12 and is supported at either end by a header 20 and a header 22.

Extending between headers 20 and 22 in concentric relation around flow tube 18 is a cylindrical capacitor electrode 24 defining an inner electrical conductor surface 26. The headers 20 and 22 are provided of insulating material such as plastic.

Any electrically conductive liquid flowing through the flow tube 18 is defined by the inner wall of tube 18 to form an outer electrical conductor surface 28. The annular space between the cylindrical surface 28 of the liquid body and the inner surface 26 of the capacitor electrode 24 comprise the dielectric insulation between the electrical conductor surfaces 26 and 28. A portion of this space is seen to be occupied by the dielectric material of the tube 18. The remainder of this annular space comprises the reaction chamber 30.

When provided as shown, an electrical force field great enough to cause arcing through the space of reaction chamber 30 can not arc through the insulation of the wall of tube 18.

Figure 2:
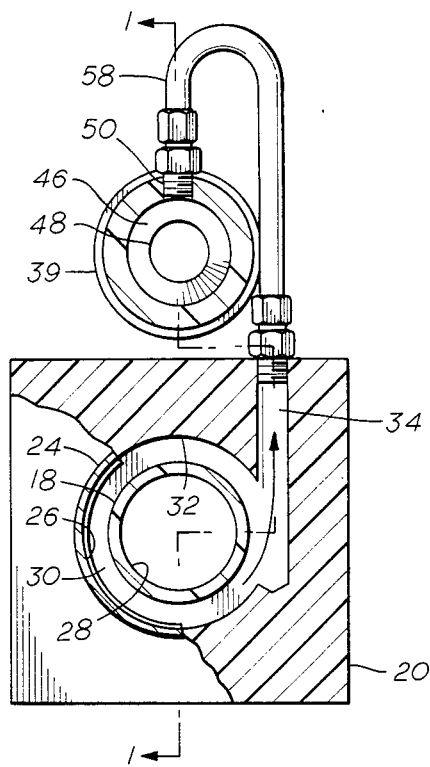
FIG. 2 is a sectional view taken along 2—2 of FIG. 1.

As shown in FIG. 2, the header 20 has been machined out to closely fit about tube 18 and also machined to receive the end of the capacitor electrode 24 in close fitting relationship. The bore receiving the capacitor electrode 24 has been counterbored slightly with a counterbore 32 which slightly extends the length of the reaction chamber 30. A passageway 34 is provided through the side of the header 22 into tangential intersection with the counterbore 32.

Figure 3:
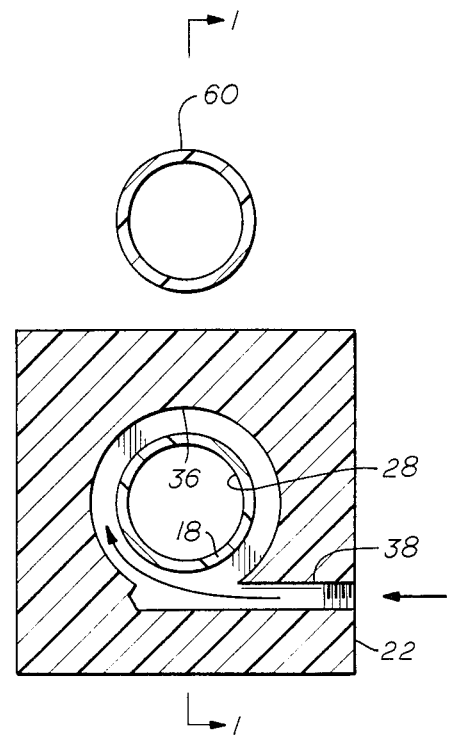
FIG. 3 is a cross-section taken along 3—3 of FIG. 1.

Referring now to FIG. 3, the header 20 is shown to be also machined as described for header 22 to receive the other end of the capacitor electrode 24 and to have a counterbore 36. A passageway 38 is provided through the side of the header 20 which intersects with counterbore 36 in tangential relationship.

It will be noted that the counterbore 32 and tangential passageway 34 are disposed in mirror image relationship with the counterbore 36 and passageway 38 such that a gas entering passageway 38 will tangentially enter the reaction chamber 30 to be rotated around within the chamber 30 in a spiral configuration and thereafter exit in tangential relationship within the counterbore 32 through the passageway 34.

The tangential entry and exit of a gaseous media, such as air, along with the spiral-like passage of the media through the reaction chamber 30, contributes to a greater resident time of the media within the reaction chamber with a designated flow rate of gaseous media into and out of the chamber and also to sweeping the reaction chamber clean of stagnant gas pockets.

As shown, the tube 18 is connected at its exit end through a 180° elbow 39 into a Venturi member 40. Venturi member 40 is comprised of two parts with the upstream part 42 defining the converging throat 44 of the Venturi and an annular groove 46 with an inner annular lip 48 disposed around the converging throat 44.

A passageway 50 is provided to extend from the annular groove 46 to outside the part 42.

The member 40 also includes a downstream part 52 which defines the expanding portion of the throat 44. The parts 42 and 52 define a socket connection which is dimensioned to provide an annular slot 54 between the lip 48 and a shoulder 56 defined on part 52 such that the slot 54 comprises the suction orifice of the Venturi with passage from the passageway 50 through the annular groove 46. The width of the slot 54 is desirably fairly close. As an example, the width of the slot 54 may be from 3/64" to 5/64".

As best shown in FIG. 2, the passageway 50 of Venturi member 40 is connected through a tube 58 and appropriate tubing fittings to the passageway 34 which extends through the header 20 into tangential communication with the reaction chamber 30.

As an illustration, water moving through the tube 18 and the Venturi member 40 at a rate of 30 g.p.m. will create a vacuum of about 19" (of water) at the annular slot 54.

Also as shown, the downstream part 52 of Venturi member 40 will extend into another section of tubing 60 similar to tube 18.

In the embodiment of the apparatus as shown in FIG. 1, the parts 18, 20, 22, 42, 52, 58 and 60 may all be provided of a dielectric plastic material such as poly-vinyl chloride (PVC). The concentric capacitor electrode 24 may be provided of a good conductor metal such as stainless steel, for example.

All of the PVC parts and the electrode 24, as specified above and shown in FIGS. 1-3, may be assembled as shown and fastened together with the cement commonly used in the assembly of PVC piping and plumbing.

The electrical system 16 as shown in FIG. 1 may be selected to operate from commonly available 60 hertz 110 V or 220 V A.C. power. The circuit includes a step-up transformer 62 having a primary winding 64 and a secondary winding or coil 66. One leg of secondary coil 66 is electrically connected to capacitor electrode 24 and the other leg of winding 66 is connected to ground. In actual construction the electrical connection to the electrode 24 has been a metal clamp fastened around electrode 24.

The electrically conductive liquid within the tube 18 and forming electrical conductor surface 28 is assured connection with ground through an electrode 68 which extends into the 180° elbow and then electrically connected to ground as indicated along with the other leg of transformer winding 66. Actually, the grounding electrode 68 could be connected directly with the second leg of the winding 66. As a safety measure, both such connections from winding 66 and electrode 68 should also be grounded as shown in the drawing.

The circuit 16 also includes a operation indicating lamp 78 and a vacuum safe switch 78 connected (not shown) to disable circuit 16 when no vacuum is being generated at Venturi orifice slot 54.

In the prototype of apparatus 10, a transformer 62 capable of generating 10,000 volts was sued, as an example. It can be seen that the conductor surfaces 26 and 28, along with reactor chamber 30 and the secondary winding 66 of the transformer 62, comprise an LC oscillator which seemed to enhance the output voltage across the conductor surfaces 26 and 28.

OPERATION OF A PREFERRED EMBODIMENT

Though the ozone generating method apparatus of the present invention may be useful when applied in a variety of situations, a most apparent application is in the sterilization and clarification of swimming pool water.

Figure 4:
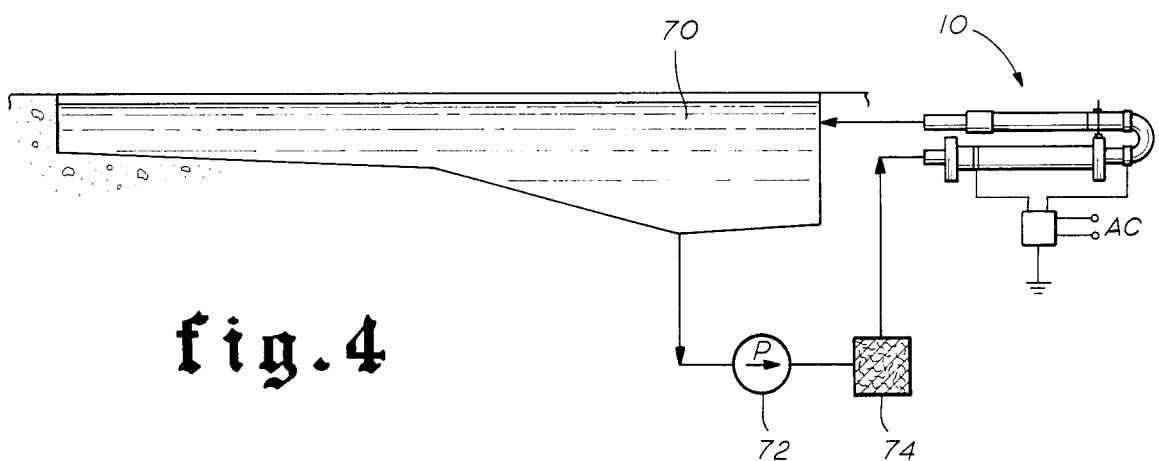
FIG. 4 is a schematic diagram illustrating an ozone and singlet oxygen generator of the present invention as incorporated into a swimming pool cleaning system, as an example.

FIG. 4 schematically shows the apparatus 10 in a swimming pool application. As shown, water is picked up from a pool 70 by a pump 72 and moved through a filter system 74 and through the apparatus 10, such as shown in FIG. 1, then back into pool 70.

As an example, the flow rate through pump 72 and generator apparatus 10 may be 30 gpm. The vacuum created within the Venturi member 40 at slot 54 draws air into the passageway 38 into a circular and spiral flow path within the reaction chamber 30.

Once the vacuum is established, an elevated electrical force field is created between the electrical conductor surface 26 and the electrical conductor surface 28 of electrical system 16. An alternating electrical current flows through the circuit including the water within tube 18, the grounding electrodes 68, the ground connection the secondary winding 66, and the capacitor electrode 24 to create the force field. Ionization occurs within the reactor chamber 30. The naturally occuring random cosmic radiation passing through reactor chamber 30 is believed to contribute to such ionization.

The resident time of the air within the reaction chamber 30 is sufficient to attain maximum ozone and singlet oxygen constituents, on the one hand, considering the rapid decay of the constituents into normally occurring oxygen ($O_2$) on the other hand. An exemplary resident time of the air within the reaction chamber 30 may be 0.1 second, for example.

The gas or air containing the constituents is moved out of reaction chamber 30 through the tangental exit of passageway 34 and thereupon moved through the tubing 60, passageway 50, annular groove 46 and the annular slot 54 into intimate mixing of the air into the water while the water is flowing past the slot 54, through the expanding part of the Venturi and the tube 60, into filter system 74, for example.

The reaction of the ozone and the singlet oxygen constituents with pathogens in the water, and to render the water sterile, is substantially immediate from the time the constituents leave the Venturi orifice slot 54.

Any excess ozone and singlet oxygen over that necessary for sterilizing the water is dissipated by reaction of the constituents with any organic matter or other oxidizable matter entrained with the water as well as the normally occuring dissipation in water.

Though the exact interaction of the ozone and singlet oxygen constituents with impurities in the water is not known precisely, it is known that the action of these constituents may serve to flocculate the impurities in the water into particles so that they may be readily removed by filtration, leaving water that is sparkling clear and free of turbidity. It may also be that the constituents oxidize insoluble material into a readily soluble state.

The generating method and apparatus as herein disclosed is useful in many other applications as previously mentioned. Almost any body of water and possibly other electrically conductive solutions may be disinfected and sterilized by the ozone and singlet oxygen constituents.

Additionally, the ionized gas, such as air, and containing the ozone and singlet oxygen constituents, can be used with powerful effect in disinfecting objects such as surgical instruments and medical containers.

Direct application of such ionized gas to human skin which carries pathogens such as seborrhea, athletes foot and related irritations as caused by fungal growth in the skin tissue has been very effective. (These constituents are toxic and should be applied by qualified medical personnel).

It should also be noted, with reference to FIG. 1, that an electrically conductive tube (not shown) may be mounted inside tube 18 in connection with ground, as through connection with electrode 68, and provide the conductor surface 28 in substitute for a conductive liquid in the operation of power circuit 16. In this event, an electrically semiconductive or nonconductive liquid, such as diesel fuel or crude oil, may be moved through the tube 18 and Venturi 40 (or Venturi 40 only) for bacteriacidal treatment. Pervasive build-up of microorganisms is presently a problem in jet fuels, for example.

It is noted that modifications and other embodiments of the invention will become obvious to those skilled in the art and that the invention as herein disclosed is to be limited only by the perview of the appended claims.

What is claimed is:

1. A method for killing pathogens contained within an electrically conductive liquid, with ozone ($O_3$) and singlet oxygen ($O_1$) comprising the steps of:

(a) providing an annular chamber defined by (1) a cylindrical body of said electrically conductive liquid forming a first electrical conductor surface, (2) a cylindrical insulated tube confining said liquid, (3) said insulated tube forming a dielectric medium, and (4) a cylindrical metal housing enclosing said tube and forming a second electrical conductor surface;

(b) establishing an elevated electrical force field in said annular chamber between said first conductor surface and said second conductor surface;

(c) moving a gas containing normally occurring oxygen ($O_2$) into, through, and out of, said chamber at a moving rate suitably slow to permit ionization within said gas as caused while said gas is within said force field and thereby to transform said normally occurring oxygen ($O_2$) into the constituents of ozone ($O_3$) and singlet oxygen ($O_1$); and, (d) mixing said gas while containing said constituents immediately with said liquid containing pathogens in a venturi for the purpose of allowing said constituents to react with and to kill said pathogens, wherein said electrically conductive liquid is pumped through said tube and said venturi, and said gas is moved out of said chamber and mixed with said liquid by a vacuum created in said venturi by the pumping of said liquid.

2. The method of claim 1 wherein said electrically conductive liquid includes organic impurities and said constituents react with said impurities and remove said impurities from said electrically conductive liquid.

3. The method of claim 1 wherein said liquid comprises swimming pool water.

4. The method of claim 1 wherein said liquid comprises water from waste water systems.

5. The method of claim 1 wherein said liquid comprises potable drinking water.

6. The method of claim 1 wherein said liquid comprises oil well treatment fluids.

7. The method of claim 1 wherein said liquid comprises hydrocarbon fluids.

8. The method of claim 1 wherein said liquid comprises cooling water such as utilized in heat exchanger cooling towers.

9. In apparatus for killing pathogens contained within an electrically conductive liquid, utilizing ozone ($O_3$) and singlet oxygen ($O_1$), the combination comprising:

(a) a flow tube including a first section and a second section for containing a flow of said liquid, each section of said sections comprising substantially cylindrical chambers of dielectric material, said sections being connected such that said conductive liquid flows through both said sections, wherein said conductive liquid comprises a first electrode within said first section;

(b) a second electrode mounted concentrically about said first section and defining an annular chamber between said first section of said flow tube and said second electrode;

(c) a means for establishing an elevated electrical force field in said annular chamber between said first electrode and said second electrode;

(d) means for moving a gas containing normally occurring oxygen ($O_2$) through said annular chamber at a suitable flow rate to permit ionization within said gas while said gas is within said annular space and thereby transforming said normally occurring oxygen ($O_2$) into the constituents of ozone ($O_3$) and singlet oxygen ($O_1$); and (e) means for mixing said gas including said ozone ($O_3$) and said singlet oxygen ($O_1$) with said conductive liquid in a venturi located in said second section and thereby to contact said gas with said pathogens contained within said liquid to react with and kill said pathogens, wherein said means for moving and said means for mixing are constructed to pump said liquid through said flow tube and said venturi to create a vacuum in said venturi and move said gas out of said annular chamber and into said venturi.

* * * * *